US005831118A

United States Patent [19]

Inagaki et al.

[11] Patent Number: 5,831,118

[45] Date of Patent: Nov. 3, 1998

[54] EPIMERIZATION OF 2- OR 4-SUBSTITUTED CYCLOHEXANECARBOXYLIC ACIDS

[75] Inventors: Takashi Inagaki; Akihito Mizutani, both of Osaka-fu, Japan

[73] Assignee: Katayama Seiyakusyo Co., Ltd., Japan

[21] Appl. No.: 876,318

[22] Filed: Jun. 16, 1997

[30] Foreign Application Priority Data

Jun. 18, 1996 [JP] Japan .................................... 8-156720
Dec. 24, 1996 [JP] Japan .................................... 8-343164

[51] Int. Cl.[6] .......................... C07B 55/00; C07C 61/08; C07C 61/09

[52] U.S. Cl. .......................... 562/401; 562/507; 562/509

[58] Field of Search .................................... 562/401, 507, 562/509

[56] References Cited

U.S. PATENT DOCUMENTS 4,948,790 8/1990 Archer et al. .......................... 514/178

FOREIGN PATENT DOCUMENTS 196222 10/1986 European Pat. Off. .
54-27546 3/1979 Japan .
56-68612 6/1981 Japan .
56-120636 9/1981 Japan .
56-125342 10/1981 Japan .
60-258141 12/1985 Japan .

OTHER PUBLICATIONS

The Merck Index 12th edition, Merck & Co., Inc., Whiehouse Station, NJ, 1996, p. 1315 compound no. 7806.
Cooke, R. G., et al, J. Chem. Soc. 1939, 1245–1247 (1939).
Inukai, T., et al, Chem. Abst. 91:20102s (1979).
Chem. Abst. 95:138635d (1981).
Chem. Abst. 96:51873b (1982).
Chem. Abst. 96:34693a (1982).
Fujimoto, M., Chem. Abst. 105:60344m (1986).

*Primary Examiner*—Gary Geist
*Assistant Examiner*—Brian J. Davis

[57] ABSTRACT

The present invention relates to a new method for obtaining a purity of about 93% to 100% of the trans form of 2- or 4-substituted cyclohexanecarboxylic acid or reactive derivatives thereof from the cis form or a mixture of the cis and trans forms by a single step, particularly, to a method for obtaining a purity of substantially 100% of the trans form of 4-substituted cyclohexanecarboxylic acid.

26 Claims, 1 Drawing Sheet

EPIMERIZATION OF 2- OR 4-SUBSTITUTED CYCLOHEXANECARBOXYLIC ACIDS

BACKGROUND OF THE INVENTION

1. Field of the Invention

The present invention relates to a new method for obtaining a purity of about 93% to 100% of the trans form of 2- or 4-substituted cyclohexanecarboxylic acid or reactive derivatives thereof from the cis form or a mixture of the cis and trans forms by a single step, particularly, to a method for obtaining a purity of substantially 100% of the trans form of 4-substituted cyclohexanecarboxylic acid.

2. Description of the Prior Art 2- or 4-substituted cyclohexanecarboxylic acid or reactive derivatives thereof are used as intermediates in a process for preparing medicines, pesticides or liquid crystals, particularly, the trans form of 4-isopropyl-cyclohexanecarboxylic acid is useful as an intermediate of a D-phenylalanine derivative which is an antidiabetic drug (Japanese Patent Publication A No. 63-54321 (1988)). And also, 4-alkyl, 4-fluorine-substituted lower alkyl- or 4-carboxy-cyclohexanecarboxylic acids are useful as intermediates of liquid crystals (cf. Japanese Patent Publication A No. 54-27456 (1989)) or medicines (cf. U.S. Pat. No. 4,948,790).

In general, 4- and 2-substituted cyclohexanecarboxylic acids have the following steric configurations, respectively.

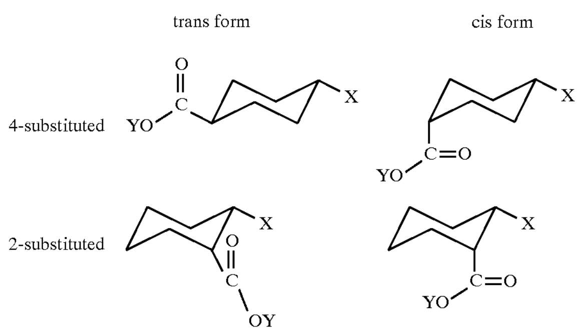

The trans form in which the substituent is present in the equatorial configuration relating to the carboxy group (Y═H) or a reactive derivative group is more stable than the cis form in which the substituent is present in an axial configuration. The cis form is known to convert into an equilibrium mixture in a ratio of trans:cis of 85:15.

For example, cuminic acid is subjected to catalytic reduction to give a mixture of the trans and cis forms of 4-isopropyl-cyclohexanecarboxylic acid in a ratio of trans:cis of 25:75. The mixture is converted by a conventional method into methyl esters, which are then epimerized by heating in the presence of sodium hydride at 150° C. to give an equilibrium mixture in a ratio of trans:cis of 85:15 (European Patent Publication A No. 0196222).

A method for epimerization is known whereby 4-isopropyl-cyclohexanecarboxylic acid is directly heated in the presence of a base. For example, cuminic acid is dissolved into sodium hydroxide and then reduced at a high temperature (200° C.) and pressure (200 atm) to give an equilibrium mixture of 4-isopropyl-cyclohexanecarboxylic acid in a ratio of trans:cis of 85:15 (cf. Japanese Patent Publication A No. 56-68612 (1981) and J. Chem. Soc., 1939, 1245–1247 (1939)). And also the epimerization of 4-substituted cyclohexanecarboxylic acids by alkaline and alkaline earth metals is known to give an equilibrium mixture in a ratio of trans:cis of 75–85:25–15 (Japanese Patent Publication A No. 60-258141 (1985)). In addition, the epimerization of 2- and 4-substituted cyclohexanecarboxylic acids by heat is known (cf. Japanese Patent Publication A No. 56-120636 (1981) and Japanese Patent publication A No. 56-125342 (1981)).

The proportion of trans-4-isopropyl-cyclohexanecarboxylic acid obtained by a conventional epimerization of the cis form only or a mixture of the cis and trans forms of 4-isopropyl-cyclohexanecarboxylic acids is 85% and therefore, the trans form has to be isolated by recrystallization to improve the purity. Then, in order to obtain the trans form in good yield, mother liquid is again epimerized and also the same procedure as above must be repeated to obtain only the trans form. Such epimerization is unsuitable as an industrial process and in poor yield.

SUMMARY OF THE INVENTION

As a result of an extensive study of epimerization of 4-lower alkyl-cyclohexanecarboxylic acid in good yield, it was found that, surprisingly, the epimerization of 4-lower alkyl-cyclohexanecarboxylic acid (trans:cis=23:77) proceeds efficiently by heating with potassium hydroxide at a temperature in the range from 130° C. to 220° C. to give the trans form in a high purity of 98.4% to 99.8%. By further experiments, 2-substituted cyclohexanecarboxylic acid can be efficiently epimerized and also, substituents are not limited to a lower alkyl group. The present invention was accomplished by the above findings.

The first aspect of the present invention is provide a method for obtaining of potassium trans-2- or 4-substituted cyclohexanecarboxylate in a purity of about 93% to about 100% by a single step which comprises treating the cis form or a mixture of the cis and trans forms of 2- or 4-substituted cyclohexanecarboxylic acid or reactive derivatives thereof with potassium hydroxide at a temperature in the range from 130° C. to about 220° C. Particularly, in case of 4-substituted cyclohexanecarboxylic acid, potassium salt of the trans form can be obtained in a purity of substantially 100% according to the method of the present invention.

The second aspect of the present invention is to provide potassium 4-isopropyl-cyclohexanecarboxylate which is obtained using the process of the present invention as described above.

The third aspect of the present invention is to provide potassium hydroxide for epimerization to obtain trans-4-isopropyl-cyclohexanecarboxylic acid in a purity of substantially 100% from the cis form or a mixture of the cis and trans forms of 4-isopropyl-cyclohexanecarboxylic acid or reactive derivatives thereof.

DETAILED DESCRIPTION OF THE PREFERRED EMBODIMENTS

Figure 1:
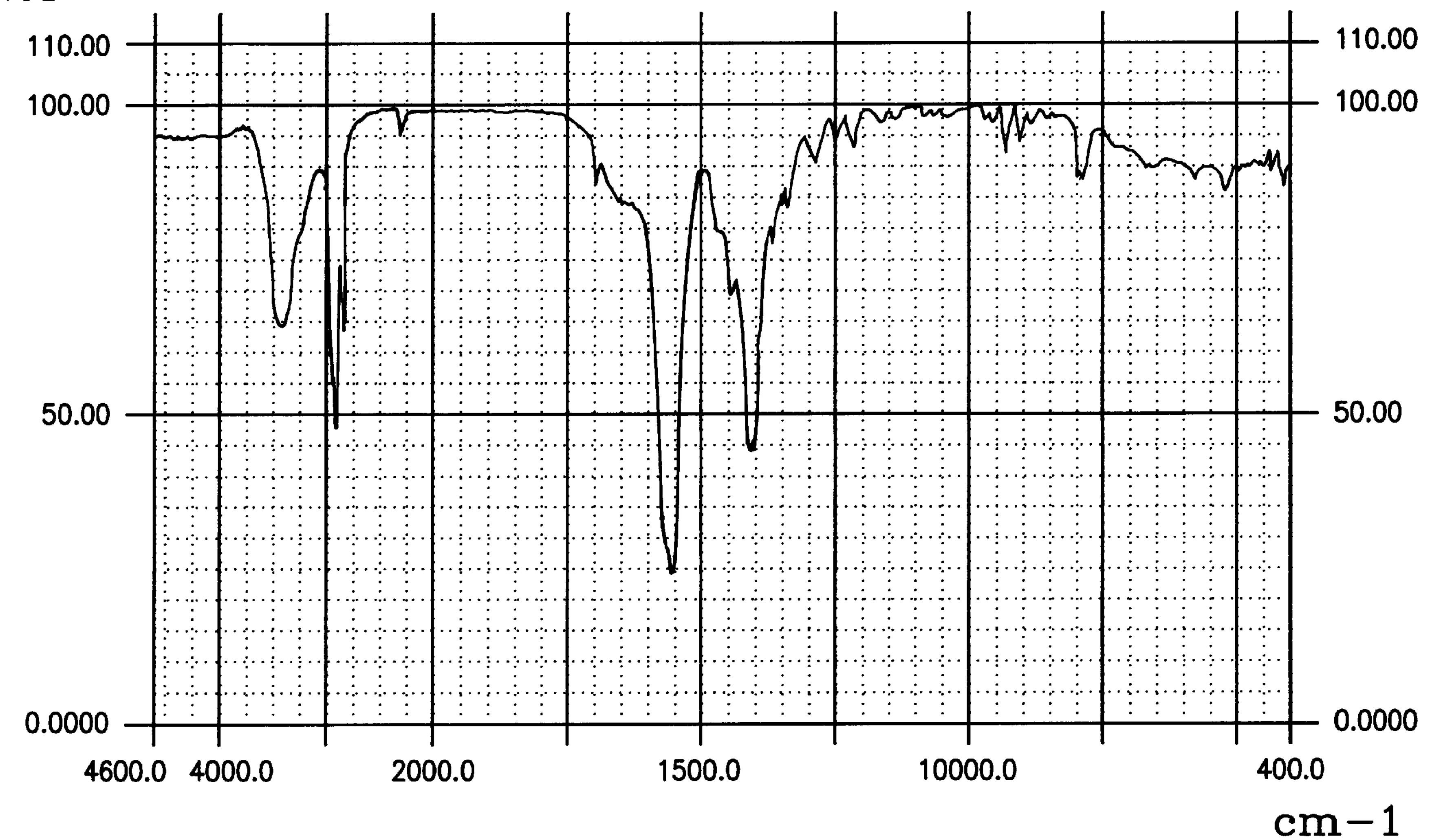
FIG. 1 depicts an IR Chart of potassium trans-4-isopropyl-cyclohexanecarboxylate after recrystallization from water, obtained by the KBr method and constitutes results of Example 4.

The term "2- or 4-substituted" means that a substituent is present at the 2 or 4 position on a cyclohexane ring relating to the carboxy group of cyclohexanecarboxylic acid.

The term "substituent" is not specifically limited, and preferably includes $C_1$ to $C_8$ alkyl, and fluorine-substituted $C_1$ to $C_5$ alkyl or carboxy groups, and $C_1$ to $C_8$ alkyls being more preferable.

The term "$C_1$ to $C_8$ alkyls" means a straight or branched, saturated hydrocarbon residues having between 1 and 8 carbon atoms, preferably between 1 and 6, most preferably, between 1 and 5. Examples of $C_1$ to $C_8$ alkyls are methyl, ethyl, propyl, isopropyl, n-butyl, iso-butyl, t-butyl, n-pentyl, isopentyl, hexyl, heptyl and octyl, preferably methyl, propyl iso-propyl, and butyl groups.

The term "fluorine-substituted $C_1$–$C_5$ alkyls" means straight or branched, saturated hydrocarbon residues having between 1 and 5 carbon atoms, in which one or more hydrogen atoms are substituted by fluorine atoms. The most preferred is the trifluoromethyl group.

The term "carboxy" means the —COOH group, however, the present invention may cover such a case in that a reactive derivative of COOH could be finally converted to COOH by treating with the potassium hydroxide used in the method of the present invention.

"2- or 4-cyclohexanecarboxylic acid derivative" means a derivative which can be converted by the potassium hydroxide used for the epimerization of the present invention, for example, a carboxylic acid protecting group which can be removed by an alkaline base, and generally, an ester derivative. In the above sense, lower alkyl esters such as methyl, ethyl and the like and optionally substituted aryl lower alkyl esters such as benzyl, p-nitrobenzyl, benzhydrile, trityl, anthranylmethyl and the like can be mentioned as a "2- or 4-cyclohexanecarboxylic acid derivative" (cf. Shin Jikken-kagaku Koza, Vol. 14, p. 2535–2544).

The base used for the epimerization of the present invention is potassium hydroxide and a base such as a hydroxide, a carbonate of alkaline metal (sodium, lithium) or alkaline earth metal (magnesium, calcium) could not efficiently advance the epimerization of the present invention.

The wording "by a single step" means to include no other step than treating with potassium hydroxide in order to increase the ratio of the trans form in a mixture ratio of cis and trans forms of 2- or 4-cyclohexanecarboxylic acid.

The wording "a purity of substantially 100%" covers from about 95% to about 100%, preferably, from about 97.5% to about 100%. After the reaction, no step is needed to increase the ratio of the trans form in a mixture ratio of cis and trans forms, and therefore, the objective compound can be obtained in high yield.

The organic solvents used herein may be any solvents having a boiling point of more than 150° C., however, it is essential that the solvents do not dissolve the potassium salt of 2- or 4-cyclohexanecarboxylic acid (the epimerization itself can proceed without any solvent). As typical examples of organic solvents, diethylene glycol diethyl ether, p-cymene, 1,3-diisopropyl benzene, mesitylene or a mixture thereof, Shellsol 71 (a commercial name, a mixture of $C_{10}$–$C_{12}$ isoparaffins, Shell Japan) can be mentioned, preferably, diethylene glycol diethyl ether, p-cymene, 1,3-diisopropyl benzene, or Shellsol 71, more preferably, in terms of the stability, safety, operability and cost of solvents, the most preferred is Shellsol 71. Epimerization can not efficiently proceed in a solvent that can dissolve the potassium salt of 2- or 4-cyclohexanecarboxylic acid, for example, water, ethylene glycol, or any solvent having a boiling point lower than about 130° C., for example, n-heptane, toluene or xylene.

The reaction temperature is higher than 130° C., preferably higher than 140° C., most preferably higher than 150° C. and also is lower than 220° C., preferably lower than 200° C., most preferably lower than 180° C.

Potassium hydroxide is used in an amount of 2 to 4 weight equivalents of 2- or 4-substituted cyclohexanecarboxylic acid, preferably 2 to 3 weight equivalents, most preferably 2 weight equivalents, while in the case of 2-carboxy- or 4-carboxycyclohexanecarboxylic acid, the base is used 4 to 8 weight equivalents, prefrably 4 to 6, and 5 weight equivalents being most preferable.

Since the end point of the reaction is monitored by a conventional method, for example, GLC analysis, the reaction period is not specified, and in general, the reaction is accomplished in 2–8 hours.

EXAMPLES

The following examples illustrate the invention and are not intended to limit the scope of the invention in any way.

Example 1

(i) 4-Isopropyl-cyclohexanecarboxylic acid (trans 27%, cis 73%) obtained from Cuminic acid (75 g, 0.46 mol) by catalytic reduction described in European Patent Publication A No. 0196222, was dissolved in Shellsol 71 (225 ml), then 53.4 g of 96% potassium hydroxide (0.91 mol) was added thereto, the reaction mixture was heated to react at 140°–150° C. for 3.5 hrs. The trans form of potassium 4-isopropyl-cyclohexanecarboxylate in the reaction mixture after epimerization was in a in-situ proportion of 98.5% by GLC analysis.

Conditions for measurement by GLC

Apparatus: GC-7AG Chromatopack CR-6A

Column: DEGS+$H_3PO_4$, (5+1%), Chromosolb W (AW) 60 mesh 2 m×ID 3 mm

Column Temp.: 100° C. to 200° C., 5° C./min

Inj. Temp.: 210° C.

Carrier gas: $N_2$

Flow rate: 35 ml/min

Inlet press.: 0.9 kg/cm$^2$ $H^2$ press.: 0.6 kg/cm$^2$

Air press.: 0.5 kg/cm$^2$

Detector: FID (ii) The reaction solution was cooled, then 50 ml of water and 100 ml of methanol were added thereto, then the mixture was left to stand followed by separation of the phases. To the lower phase (methanol/water), 95.3 g of concentrated hydrochloric acid (0.91 mol) was added dropwise at an internal temperature in the range of from 0° C. to 5° C. under cooling. After the addition, the resulting mixture was stirred at the same temperature for about 1 hr. The precipitated crystals were filtered off, dispersed to wash in 100 ml of water at a room temperature, filtered and dried to give 75.4 g of trans-4-isopropyl-cyclohexanecarboxylic acid (Purity: 99.4%, Yield: 97%).

Example 2

An epimerization reaction of 4-isopropyl-cyclohexanecarboxylic acid was performed according to the same procedure as described in Example 1, except that, instead of Shellsol 71, the various solvents shown in Table 1 were employed using the reaction times and temperatures also shown in Table 1. The results are shown in Table 1 below.

TABLE 1

| Exp. No. | Solvent | Temp. (°C.) | Time (hr) | In-situ proportion of trans form (%) |
|---|---|---|---|---|
| 1 | diethylene glycol diethylether | 145–165 | 7 | 99.6 |
| 2 | P-cymene | 140–150 | 5.8 | 98.4 |
| 3 | 1,3-diisopropyl-benzene | 138–153 | 6.8 | 98.6 |
| 4 | mesitylene | 133–139 | 3.5 | 95.1 |
| 5 | ethylene glycol | 150 | 39.8 | 79.0 |
| 6 | xylene | 120–133 | 4.9 | 35.4 |
| 7 | water | 170 (in autoclave) | 7 | 43.2 |
| 8 | n-heptane | 92–97 | 3.9 | 25.4 |
| 9 | none | 135–146 | 7 | 97.5 |

Example 3

The epimerization of 4-isopropyl-cyclohexanecarboxylic acid (trans 27%, cis 73%) was performed according to the same procedure as described in Example 1, except that, instead of potassium hydroxide, the various inorganic bases shown in Table 2 were employed using the various reaction times and reaction temperatures also shown in Table 2. The results are shown in Table 2 below.

TABLE 2

| Exp. No. | Base | Temp. (°C.) | Time (hr) | In-situ proportion of trans form (%) |
|---|---|---|---|---|
| 1 | sodium hydroxide | 150–160 | 4.8 | 30.4 |
| 2 | lithium hydroxide monohydrate | 110–118 | 7.3 | 29.0 |
| 3 | lithium hydroxide | 120–162 | 4 | 32.6 |
| 4 | barium hydroxide | 150–160 | 4 | 32.4 |
| 5 | calcium oxide | 150 | 5.4 | 40.5 |

Example 4

The reaction solution, which was obtained by following the same procedure as described in Example 1 (i), was cooled to room temperature, the precipitated crystals in the reaction mixture were filtered off, n-heptane was added thereto to wash the crystals and to give crude potassium trans-4-isopropyl-cyclohexanecarboxylate (wet weight: 130 g). 150 ml of Water was added to dissolve the crude product, the resulting solution was cooled and 97.6 g of conc. hydrochloric acid was added dropwise thereto under cooling, the precipitate was filtered off to give crude trans-4-isopropyl-cyclohexanecarboxylic acid (wet weight: 98.8 g).

To the precipitate, 97.8 g of methanol was added and heated to dissolve the precipitate at 50° C. The mixture was then filtered, 75.2 g of water was added to the filtrate, the resulting solution was heated to dissolve the filtrate and then cooled. The precipitate was filtered off to give 70 g of trans-4-isopropyl-cyclohexanecarboxylic acid (Purity by GLC analysis: 99.8% ) in a yield of 90%.

IR and NMR data for the potassium trans-4-isopropyl-cyclohexanecarboxylate (recrystallization from water) were shown as follows.

IR(KBr)$cm^{-1}$: 3423, 2934, 1558, 1408, 1285, 1215, 928

NMR($CD_3OD$-$D_2O$)δppm: 0.88(6H, J=8Hz), 0.95–2.70 (12H, m)

An IR tracing for potassium trans-4-isopropyl-cyclohexanecarboxylate is depicted in FIG. 1.

Example 5

(i) Methyl 4-isopropyl-cyclohexanecarboxylate (trans 27%, cis 73%), obtained from methyl cuminate (50 g, 0.46 mol) by the catalytic reduction described in European Patent Publication A No. 0196222, was dissolved in 158 ml of Shellsol 71, then 35.5 g of 96% potassium hydroxide was added thereto. After heating the resultant solution at 110°–120° C. for 1 hr. 5 g of water was added thereto, then heated to react at 140°–150° C. for 3.5 hrs. The trans form of potassium 4-isopropyl-cyclohexanecarboxylate in the reaction mixture after epimerization was in an in-situ purity of 98.9% by GLC analysis.

(ii) The reaction solution was cooled, then 30 ml of water and 60 ml of methanol were added thereto, then the mixture was left to stand followed by separation of the phases. To the lower phase (methanol/water), 57.2 g of concentrated hydrochloric acid (0.55 mol) was added dropwise at an internal temperature in the range of from 0° C. to 5° C. under cooling. After the addition, the resulting mixture was stirred at the same temperature for about 1 hr. The precipitated crystals were filtered off, dispersed to wash in 60 ml of water at room temperature, filtered and dried to give 44.8 g of trans-isopropyl-cyclohexanecarboxylic acid (Purity 99.5%, Yield 94%).

Example 6

Trans-4-isopropyl-cyclohexanecarboxylic acid (46.2 g) was obtained from 60 g of isopropyl cuminate in the same manner as described in Example 5 (Purity 99.5%, Yield 93.3%).

Example 7

(i) 4-Methyl-cyclohexanecarboxylic acid (trans 32.2%, cis 67.8%) obtained from 10 g of p-toluic acid (0.073 mol) by catalytic reduction as described in European Patent Publication A No. 0196222, was dissolved in 35 ml of Shellsol 71, then 8.5 g of 96% potassium hydroxide (0.15 mol) was added thereto, the reaction mixture was heated to react at 140°–150° C. for 3.5 hrs. After completion of the reaction, the in-situ purity of the trans form was found to be 95.8% by GLC analysis.

(ii) The reaction solution was cooled, then 8 ml of water and 16 ml of methanol were added thereto, then the mixture was left to stand followed by separation of the phases. To the lower phase (methanol/water), 15.2 g of concentrated hydrochloric acid (0.15 mol) was added dropwise at an internal temperature in the range of from 0° C. to 5° C. under cooling. After the addition, the resulting mixture was stirred at the same temperature for about 1 hr. The precipitated crystals were filtered off, dispersed to wash in 16 ml of water at a room temperature, filtered and dried to give 9.4 g of trans-4-methyl-cyclohexanecarboxylic acid (Purity: 96.2%, Yield: 90.0%). The trans-4-methyl-cyclohexanecarboxylic acid obtained above was recrystallized from water/methanol to give the same in a purity of 99.99%.

m.p. 111°–112° C.

Example 8

(i) 4-n-Propyl-cyclohexanecarboxylic acid (trans 42.3%, cis 56.6%) obtained from 10.0 g of 4-n-propyl benzoic acid (0.061 mol) by catalytic reduction described in European Patent Publication A No. 0196222, was dissolved in 30 ml of Shellsol 71, then 7.1 g of 96% potassium hydroxide (0.12 mol) was added thereto, the reaction mixture was heated to react at 140°–150° C. for 3.5 hrs. After completion of the reaction, the in-situ purity of the trans form was found to be 99.2% by GLC analysis.

(ii) The reaction solution was cooled, then 7 ml of water and 14 ml of methanol were added thereto, then the mixture was left to stand followed by separation of the phases. To the lower phase (methanol/water), 12.7 g of concentrated hydrochloric acid (0.12 mol) was added dropwise at an internal temperature in the range of from 0° C. to 5° C. under cooling. After the addition, the resulting mixture was stirred at the same temperature for about 1 hr. The resulting crystals were filtered off, dispersed to wash in 13 ml of water at a room temperature, filtered and dried to give 9.7 g of trans-4-propyl-cyclohexanecarboxylic acid (Purity 99.6%, Yield 93.6%).

m.p.: 97°–98° C.

Example 9

(i) 4-n-Butyl-cyclohexanecarboxylic acid (trans 41.1%, cis 54.7%) obtained from 10.0 g of 4-n-butyl benzoic acid (0.056 mol) by catalytic reduction described in European Patent Publication A No. 0196222, was dissolved in 30 ml of Shellsol 71, then 6.1 g of potassium hydroxide (0.11 mol) was added thereto, the reaction mixture was heated to react at 140°–150° C. for 3.5 hrs. After completion of the reaction, The in-situ purity of the trans form was found to be 97.7% by GLC analysis.

(ii) The reaction solution was cooled, then 6 ml of water and 12 ml of methanol were added thereto, then the mixture was left to stand followed by separation of the phases. To the lower phase (methanol/water), 11.4 g of concentrated hydrochloric acid (0.11 mol) was added dropwise at an internal temperature in the range of from 0° C. to 5° C. under cooling. After the addition, the resulting mixture was stirred at the same temperature for about 1 hr. The precipitated crystals were filtered off, dispersed to wash in 12 ml of water at a room temperature, filtered and dried to give 9.1 g of trans-4-butyl-cyclohexanecarboxylic acid (Purity 99.5%, Yield 88.0%).

m.p.: 36°–37° C.

The results of Examples 7–9 are shown in Table 3 below.

TABLE 3

| Example No. | R-Substituted benzoic acid | In-situ ratio after catalytic reduction (trans %:cis %) | In-situ proportion of trans form after epimerization (%) |
|---|---|---|---|
| 7 | 4-$CH_3$ | 32.3:67.8 | 95.8 |
| 8 | 4-n-$C_3H_7$ | 42.3:56.6 | 99.2 |
| 9 | 4-n-$C_4H_9$ | 41.1:54.7 | 97.7 |

| Example No. | Isolated crude product (trans %) | Purified product (trans %) | m.p. (°C.) |
|---|---|---|---|
| 7 | 96.2 | >99.99 | 111–112 |
| 8 | 99.6 | — | 97–98 |
| 9 | 99.5 | — | 36–37 |

Example 10

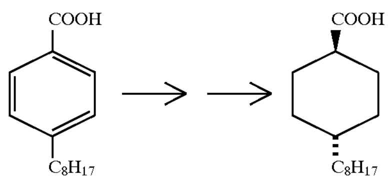

(i) 4-n-Octyl cyclohexanecarboxylic acid (trans 42.0%, cis 58.0%) obtained from 10.0 g of 4-n-octyl benzoic acid (0.043 mol) by catalytic reduction described in European Patent Publication A No. 0196222, was dissolved in 20 ml of Shellsol 71, then 5.0 g of 96% potassium hydroxide solution (0.085 mol) was added thereto, the reaction mixture was heated to react at 140°–150° C. for 3.5 hrs. After completion of the reaction, the in-situ purity of the trans form was found to be 98.5% by GLC.

(ii) The reaction solution was cooled, then 5 ml of water and 10 ml of methanol were added thereto, then the mixture was left to stand followed by separation of the phases. To the lower phase (methanol/water), 8.86 g of concentrated hydrochloric acid (0.085 mol) was added dropwise at an internal temperature in the range of from 0° C. to 5° C. under cooling. After the addition, the resulting mixture was stirred at the same temperature for about 1 hr. The precipitated crystals were filtered off, dispersed to wash in 10 ml of water at a room temperature, filtered and dried to give 9.0 g of trans-4-n-octyl-cyclohexanecarboxylic acid (Purity 99.5%, Yield 88.5%).

m.p. 36°–37° C.

Example 11

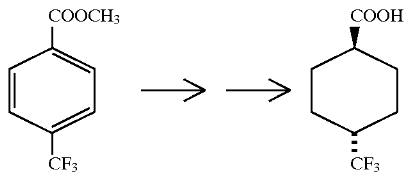

(i) To 20.4 g of methyl 4-trifluoromethylcyclohexanecarboxylate (trans 23.4%, cis 76.6%) obtained from 20.0 g of methyl 4-trifluoromethylbenzoate (20 g, 0.105 mol) by catalytic reduction, 80 ml of Shellsol 71, 15 ml of methanol, 15 ml of water and 12.3 g of 96% potassium hydroxide (0.21 mol) were added. The resulting mixture was heated to react at 175°–180° C. for 10 hrs while distilling off the water formed. After completion of the reaction, the in-situ purity of the trans form of 4-trifluoromethylcyclohexanecarboxylic acid was found to be 95.0% by HPLC.

Conditions for measurement by HPLC

Column: ODS-TSKGel-80TM

Mobile phase: 0.02M phosphate buffer (pH 2.5)/acetonitrile (70/30)

Detection: 210 nm

Flow rate: 1.0 ml/min (ii) The reaction solution was cooled, then 11.4 ml of water and 23 ml of methanol were added thereto, then the mixture was left to stand followed by separation of the phases. To the lower phase (methanol/water), 21.8 g of concentrated hydrochloric acid (0.21 mol) was added dropwise at an internal temperature in the range of from 0° C. to 5° C. under cooling. After the addition, the resulting mixture was stirred at the same temperature for about 1 hr. The precipitated crystals were filtered off, dispersed to wash in 23 ml of water at a room temperature, filtered and dried to give 14.6 g of trans-4-trifluoro-methyl-cyclohexanecarboxylic acid (Purity 99.5%, Yield 82.2%).

m.p. 155°–156° C.

Example 12

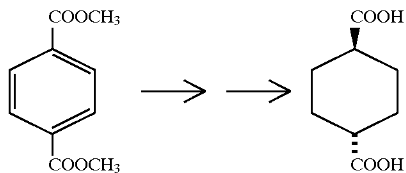

(i) Dimethyl 1,4-cyclohexane-dicarboxylate (25.5 g) (trans 46.5%, cis 53.5%, which was obtained from 25 g of dimethyl terephthalate (0.128 mol) by catalytic reduction, was dissolved in 140 ml of Shellsol 71 and then 30 ml of methanol, 30 ml of water and 30 g of 96% potassium hydroxide (1.028 mol) were added thereto. The resulting mixture was heated to react at 140°–145° C. for 4.5 hrs while distilling off the water formed. After completion of the reaction, the in-situ purity of the trans form of 1,4-cyclohexane dicarboxylic acid was found to be 98.6% by HPLC.

The conditions for measurement were the same as in Example 11 except that the mobile phase was 0.02M phosphate buffer (pH 2.5)/acetonitrile (80/20).

(ii) The reaction solution was cooled, then 14 ml of water and 28 ml of methanol were added thereto, then the mixture was left to stand followed by separation of the phases. To the lower phase (methanol/water), 106 g of concentrated hydrochloric acid (1.02 mol) was added dropwise at an internal temperature in the range of from 0° C. to 5° C. under cooling. After the addition, the resulting mixture was stirred at the same temperature for about 1 hr. The precipitated crystals were filtered off, dispersed to wash in 28 ml of water at a room temperature, filtered and dried to give 38.8 g of trans-1,4-cyclohexane dicarboxylic acid (Purity 99.5%, Yield 90%).

m.p. >300° C.

Example 13

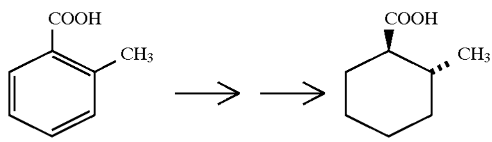

(i) To 17.6 g of 2-methyl-cyclohexanecarboxylic acid (trans 7.6%, cis 92.4%) obtained from 15.0 g of 2-methyl benzoic acid (0.11 mol) by catalytic reduction, 140 ml of Shellsol 71, 15 ml of water, 15 ml of methanol and 12.9 g of 96% potassium hydroxide (0.22 mol) were added. The resulting mixture was heated to react at 180°–190° C. for 24 hrs while distilling off the water formed. The in-situ purity of the trans form of 2-methyl-cyclohexanecarboxylic acid was found to be 93% by HPLC. The conditions for measurement were the same as described in Example 11.

(ii) The reaction solution was cooled, then 12 ml of water and 24 ml of methanol were added thereto, then the mixture was left to stand followed by separation of the phases. To the lower phase (methanol/water), 22.8 g of concentrated hydrochloric acid (0.22 mol) was added dropwise at an internal temperature in the range of from 0° C. to 5° C. under cooling. After the addition, the resulting mixture was stirred at the same temperature for about 1 hr. The precipitated crystals were filtered off, dispersed to wash in 24 ml of water at a room temperature, filtered and dried to give 12.0 g of trans-2-methyl-cyclohexanecarboxylic acid (Purity 98.0%, Yield 77.7%).

The above obtained trans-2-methyl-cyclohexanecarboxylic acid was recrystallized from petroleum ether to give the same in a purity of 99.5%.

m.p. 51°–53° C.

Example 14

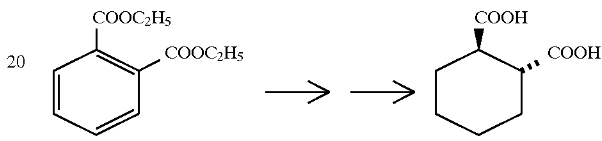

(i) To 33.6 g of diethyl 1,2-cyclohexane dicarboxylate (trans 47%, cis 53%) obtained from 30 g of diethyl phthalate (0.135 mol) by catalytic reduction, 140 ml of Shellsol 71, 16 ml of methanol, 30 ml of water and 31.5 g of 96% potassium hydroxide (0.54 mol) were added. The resulting mixture was heated to react at 140°–150° C. for 12 hrs while distilling off the water formed. The in-situ purity of the trans form of 1,2-cyclohexane dicarboxylic acid was found to be 93.5% by HPLC. The conditions for measurement by HPLC were the same as described in Example 12.

(ii) The reaction solution was cooled, then 15 ml of water and 30 ml of methanol were added thereto, then the mixture was left to stand followed by separation of the phases. To the lower phase (methanol/water), 55.6 g of concentrated hydrochloric acid (0.53 mol) was added dropwise at an internal temperature in the range of from 0° C. to 5° C. under cooling. After the addition, the resulting mixture was stirred at the same temperature for about 1 hr. The precipitated crystals were filtered off, dispersed to wash in 30 ml of water at a room temperature, filtered and dried to give 18.4 g of trans-2-cyclohexane dicarboxylic acid (Purity 97.5%, Yield 81%).

The above obtained trans-1,2-cyclohexane dicarboxylic acid was dispersed and washed in acetone to give the same in a purity of 99.6%.

m.p. 228°–230° C.

TABLE 4

| Example No. | R-Substituted benzoic acid | In-situ ratio after catalytic reduction (trans %:cis %) | In-situ purity after epimerization (trans %) |
|---|---|---|---|
| 10 | 4-$C_8H_{17}$ | 42.0:58.0 | 98.5 |
| 11 | 4-$CF_3$ | 23.4:76.6 | 95.0 |
| 12 | 4-COOH | 46.5:53.5 | 98.6 |
| 13 | 2-$CH_3$ | 7.6:92.4 | 93.0 |
| 14 | 2-COOH | 47:53 | 93.5 |

| Example No. | Isolated crude product (trans %) | Purified product (trans %) | m.p. (°C.) |
|---|---|---|---|
| 10 | 99.5 | — | 36 –37 |
| 11 | 99.5 | — | 155 –156 |

TABLE 4-continued

| | | | |
|---|---|---|---|
| 12 | 99.5 | — | >300 |
| 13 | 98.0 | 99.5 | 51 –53 |
| 14 | 97.5 | 99.6 | 228 –230 |

What is claimed is:

1. A method for obtaining of potassium trans-2- or 4-substituted cyclohexanecarboxylate in a purity of about 93% to about 100% by a single step which comprises treating the cis form or a mixture of the cis and trans forms of 2- or 4-substituted cyclohexanecarboxylic acids or derivatives thereof with potassium hydroxide at a temperature in the range from 130° C. to 220° C.

2. The method according to claim 1, wherein substitution on cis and trans forms of 2- or 4-substituted cyclohexanecarboxylic acids is with substituent selected from $C_1$–$C_8$ alkyl, fluorine-substituted $C_1$–$C_5$ alkyl and carboxy groups.

3. The method according to claim 1, wherein substitution on the cis and trans forms of 2- or 4-substituted cyclohexanecarboxylic acids is with substituent selected from methyl, propyl, isopropyl, butyl, octyl, trifluoromethyl and carboxy groups.

4. The method according to claim 1, wherein said potassium hydroxide is used in an amount of 2–8 weight equivalents of the 2- or 4-substituted cyclohexanecarboxylic acid or a derivative thereof.

5. The method according to claim 1, wherein, when said step proceeds in a organic solvent, said organic solvent does not dissolve potassium 2- or 4-substituted cyclohexanecarboxylate.

6. The method according to claim 1, wherein, when said step proceeds in a organic solvent, said organic solvent does not dissolve potassium 2- or 4-substituted cyclohexanecarboxylate and its boiling point is more than 150° C.

7. The method according to claim 2, wherein, when said step proceeds in a organic solvent, said organic solvent does not dissolve potassium 2- or 4-substituted cyclohexanecarboxylate and its boiling point is more than 150° C.

8. The method according to claim 3, wherein, when said step proceeds in a organic solvent, said organic solvent does not dissolve potassium 2- or 4-substituted cyclohexanecarboxylate and its boiling point is more than 150° C.

9. The method according to claim 4, wherein, when said step proceeds in a organic solvent, said organic solvent does not dissolve potassium 2- or 4-substituted cyclohexanecarboxylate and its boiling point is more than 150° C.

10. A method for obtaining potassium trans-4-substituted cyclohexanecarboxylate in a purity of substantially 100% by a single step which comprises treating the cis form or a mixture of the cis and trans forms of 4-substituted cyclohexanecarboxylic acids or derivatives thereof with potassium hydroxide at a temperature in the range from about 130° C. to about 220° C.

11. The method according to claim 10, wherein substitution on the cis and trans forms of 4-substituted cyclohexanecarboxylic acids is with substituent selected from $C_1$–$C_8$ alkyl, fluorine-substituted $C_1$–$C_5$ alkyl and carboxy groups.

12. The method according to claim 10, wherein substitution on the cis and trans forms of 4-substituted cyclohexanecarboxylic acids is with substituent selected from methyl, propyl, isopropyl, butyl, octyl, trifluoromethyl and carboxy groups.

13. The method according to claim 10, wherein said potassium hydroxide is used in an amount of 2–8 weight equivalents of the 4-substituted cyclohexanecarboxylic acid or a derivative thereof.

14. The method according to claim 10, wherein, when said step proceeds in a organic solvent, said organic solvent does not dissolve potassium 4-substituted cyclohexanecarboxylate.

15. The method according to claim 10, wherein, when said step proceeds in a organic solvent, said organic solvent does not dissolve potassium 4-substituted cyclohexanecarboxylate and its boiling point is more than 150° C.

16. The method according to claim 11, wherein, when said step proceeds in a organic solvent, said organic solvent does not dissolve potassium 4-substituted cyclohexanecarboxylate and its boiling point is more than 150° C.

17. The method according to claim 12, wherein, when said step proceeds in a organic solvent, said organic solvent does not dissolve potassium 4-substituted cyclohexanecarboxylate and its boiling point is more than 150° C.

18. The method according to claim 13, wherein, when said step proceeds in a organic solvent, said organic solvent does not dissolve potassium 4-substituted cyclohexanecarboxylate and its boiling point is more than 150° C.

19. The method of claim 1, wherein the treating is carried out in the absence of water.

20. The method of claim 19, wherein the treating is carried out under atmospheric pressure.

21. The method of claim 6, wherein the treating is carried out in the absence of water.

22. The method of claim 21, wherein the treating is carried out under atmospheric pressure.

23. The method of claim 10, wherein the treating is carried out in the absence of water.

24. The method of claim 23, wherein the treating is carried out under atmospheric pressure.

25. The method of claim 15, wherein the treating is carried out in the absence of water.

26. The method of claim 25, wherein the treating is carried out under atmospheric pressure.

* * * * *